United States Patent
Hutt et al.

(10) Patent No.: US 7,023,538 B2
(45) Date of Patent: Apr. 4, 2006

(54) MONITORING AN OPTICAL ELEMENT OF A PROCESSING HEAD OF A THERMAL MACHINE TOOL

(75) Inventors: Jochen Hutt, Schramberg (DE); Rainer Flaig, Eschbronn (DE)

(73) Assignee: TRUMPF Laser GmbH & Co. KG, Schramberg (DE)

(*) Notice: Subject to any disclaimer, the term of this patent is extended or adjusted under 35 U.S.C. 154(b) by 257 days.

(21) Appl. No.: 10/418,306

(22) Filed: Apr. 18, 2003

(65) Prior Publication Data

US 2004/0008342 A1 Jan. 15, 2004

(30) Foreign Application Priority Data

Apr. 20, 2002 (EP) .................................. 02008885

(51) Int. Cl.
*G01N 21/88* (2006.01)
(52) U.S. Cl. .................................................. 356/237.1
(58) Field of Classification Search ........... 219/121.75, 219/121.76, 121.6; 356/237.1–237.6, 600–613
See application file for complete search history.

(56) References Cited

U.S. PATENT DOCUMENTS

| 3,571,554 A | 3/1971 | Baujoin et al. |
| 6,118,527 A | 9/2000 | Jurca |
| 6,370,171 B1 | 4/2002 | Horn et al. |

FOREIGN PATENT DOCUMENTS

| DE | 3807873 | 9/1988 |
| DE | 19631059 | 2/1998 |
| DE | 19636249 | 3/1998 |
| DE | 19839930 | 9/2000 |
| DE | 10040912 | 4/2002 |
| EP | 0988916 | 4/2002 |
| JP | 01186296 | 7/1995 |

*Primary Examiner*—Tu T. Nguyen
(74) *Attorney, Agent, or Firm*—Fish & Richardson P.C.

(57) ABSTRACT

An apparatus for monitoring an optical element of a processing head of a machine for thermal processing of a workpiece includes a light source for coupling a light beam into an optical surface of an optical element and a detector for detecting a portion of the light beam scattered in the region of the optical surface facing the workpiece.

8 Claims, 3 Drawing Sheets

MONITORING AN OPTICAL ELEMENT OF A PROCESSING HEAD OF A THERMAL MACHINE TOOL

CLAIM OF PRIORITY

This application claims priority under 35 USC § 119(a) to European Patent application number 02008885.2-1262, filed Apr. 20, 2002, the entire contents of which are hereby incorporated by reference.

TECHNICAL FIELD

This invention relates to optical monitoring devices, and more particularly to devices for monitoring an optical element of a processing head of a thermal machine tool.

BACKGROUND

For processing workpieces by a machine for thermal welding or cutting, in particular a laser processing machine, splashes and smoke are produced in the processing region of the workpiece. The splashes and smoke can deposit on an optical surface, facing the workpiece, of an optical element of the processing head of the machine and soil the optical element. Splashes can burn into the optical surface. Smoke is deposited on the optical surface and can be removed from the optical surface to a certain degree. Deposits or damage to the optical surface produce increased absorption of laser radiation. Consequently, the thermal load of the optical element is increased which produces in the end a noticeable reduction of the laser performance available in the processing region. For heavy soiling, in particular through splashes, the increased absorption of laser radiation could destroy the optical element.

Consequently, early detection of splashes or smoke on the optical element is required to ensure constant thermal output in the working region of the workpiece and prevent destruction of the optical element by switching off the machine in due time for thermal processing, or when cleaning or replacement of the optical element is indicated.

Japanese patent number JP 01186296 A, discloses detection of a deflection or scattering of laser beams by means of detectors disposed on the side of the optical element.

German patent number DE 198 39 930 C1, describes the use of an additional light source with a light beam coupled on one side of the optical element and exiting on the other opposite side of the optical element. The intensity of a light beam of the additional light source is measured like a light barrier. A decrease in intensity means increasing thermal load of the optical element. This permits detection mainly of inner material defects such as cracks.

Further conventional measures include monitoring of the start of destruction of the optical element through an optical signal (light flash) according to European patent number EP 0 988 916 A1, or by an acoustic signal (cracking) according to German patent number DE 196 36 249 A1.

Conventionally, the thermal radiation emitted by the optical element may be detected (see, e.g., DE 3807873). However, the protecting glass may be destroyed before the temperature detector reacts due to the poor thermal conductivity of glass.

SUMMARY OF THE INVENTION

In a first aspect, an apparatus for monitoring an optical element of a processing head of a machine for thermal processing of a workpiece includes a light source for coupling a light beam into an optical surface of an optical element, and a detector for detecting a portion of the light beam scattered in the region of the optical surface facing the workpiece.

One or more of the following features may be included. The optical surface into which the light beam is coupled can face away from the workpiece. The detector can be disposed on one side of the optical element and the light source disposed on the other side of the optical element. The detector can be disposed in proximity with the optical surface on the side of the optical element opposite from the workpiece. The apparatus may further include a second detector for detecting a portion of the light beam scattered in the region of the optical surface facing the workpiece. The apparatus may include a second light source for coupling a second light beam into an optical surface of the optical element. The apparatus may include a cartridge adapted for insertion into and withdrawal from the processing head of the machine and adapted for holding the optical element, wherein the light source and the detector are disposed on the cartridge. The apparatus may further include electronics for evaluating the intensity of the scattered light beam, and the electronics can be disposed on the cartridge.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like reference symbols in the various drawings indicate like elements.

DETAILED DESCRIPTION

It is desirable to further improve detection of soiling of the optical element of the processing head of a machine for thermal processing of a workpiece.

This objective may be achieved by using an apparatus to monitor an optical element of a processing head of a machine for thermal processing of a workpiece, in particular a laser processing machine, that includes a separate light source for coupling a light beam into the optical element on the optical surface facing away from a workpiece or on a lateral edge or on a lateral surface and a detector for detecting a light beam reflected or scattered in the region of the optical surface facing the workpiece. The relevant region of the workpiece includes the optical surface itself, the volume or material interior behind the surface and also particles deposited or burnt into this region. Soiling of the optical surface facing a workpiece can be detected and displayed independently of the process parameters. The optical element can be monitored during processing or also during a processing break. The soiling changes the reflection or refractive behavior of the optical element, and this change indicates the soiling of the optical surface.

Detection of the reflected light beam is possible by at least two alternatives: arrangement of a detector on the side of the optical element or arrangement in the region of the optical surface facing away from the workpiece. The first alternative permits monitoring of deposit of splashes. The second alternative permits monitoring of deposit of splashes or formation of smoke. The use of several detectors and/or several light sources permits larger regions and different sides of the optical surface to be scanned and monitored.

A cartridge or drawer can be inserted into and withdrawn from a processing head of the machine to hold the optical element wherein the light source and the detector are mounted to the cartridge. This substantially facilitates replacement of the optical element and/or associated elements for monitoring.

The electronics for evaluating the intensity of the reflected light beam may also be disposed on the cartridge. The mounting is advantageous with regard to reduction of the sensitivity of the measuring method to disturbances. The arrangement also permits reduction of the cable length. The electronics may also comprise a storage means for correction data/characteristic lines.

A light source, detector, and electronics for signal evaluation may form a modular unit that may be disposed as structural group on or in the cartridge and can thereby be removed or supplied to the processing head in the form of a module which can be calibrated. When the module is inserted, the required electrical or mechanical contacts are automatically produced through plug connections.

Figure 1:
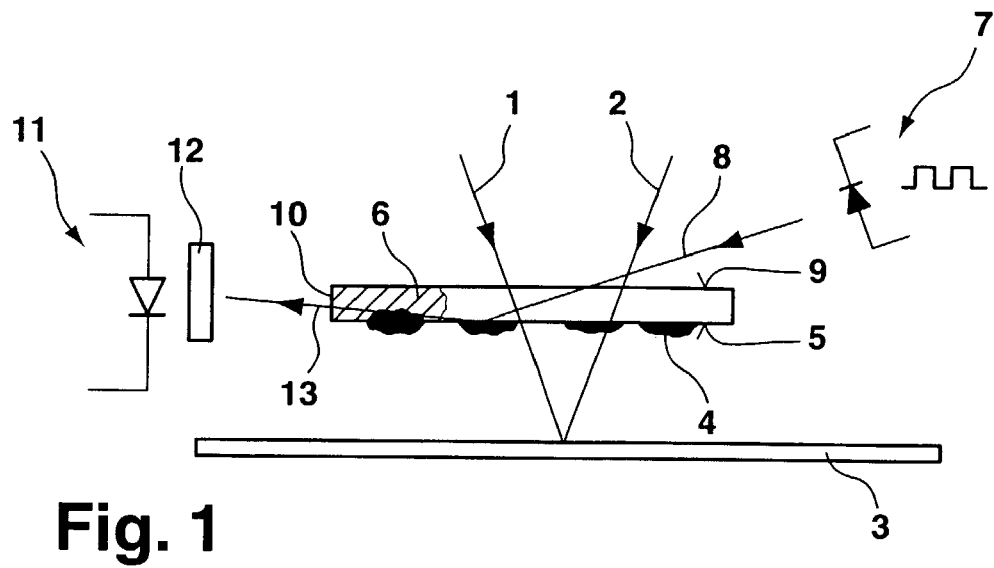
FIG. 1 is a side view of an apparatus for monitoring the deposit of splashes on an optical surface of a protecting glass of a laser processing machine.

Referring to FIG. 1, focused laser beams 1 and 2 of a laser, e.g., a YAG laser, from a processing head (not shown in detail) of a laser processing machine hit a workpiece 3 for processing. The processing of the workpiece 3 produces splashes 4 that deposit on an optical surface 5 of an optical element and are partially burnt into the surface 5 of the optical element which is formed by a protecting glass 6. The splashes 4 weaken the processing beam. The processing result of the workpiece 3 is deteriorated. Further, structural components of the processing head would be exposed to increased stress if processing of the workpiece would be continued despite deposited and/or burnt-in splashes 4. An additional light source 7 is provided for monitoring the splash deposits to couple a modulated light beam 8 into the protecting glass 6. Modulation also serves to distinguish the light beam 8 from the laser beams 1 and 2. The light beam 8 coupled to the optical surface 9 facing away from the workpiece 3 is reflected to a side surface 10 of the protecting glass 6 and detected by the detector 11 wherein a filter 12, e.g. for YAG light, is connected upstream of the detector 11. The intensity of the reflected light beam 13 can be evaluated as a measure of the deposit of splashes by a downstream electronics to interrupt processing of the workpiece when a limiting value has been exceeded, and replace the protecting glass 6 or indicate that cleaning is required.

Figure 2:
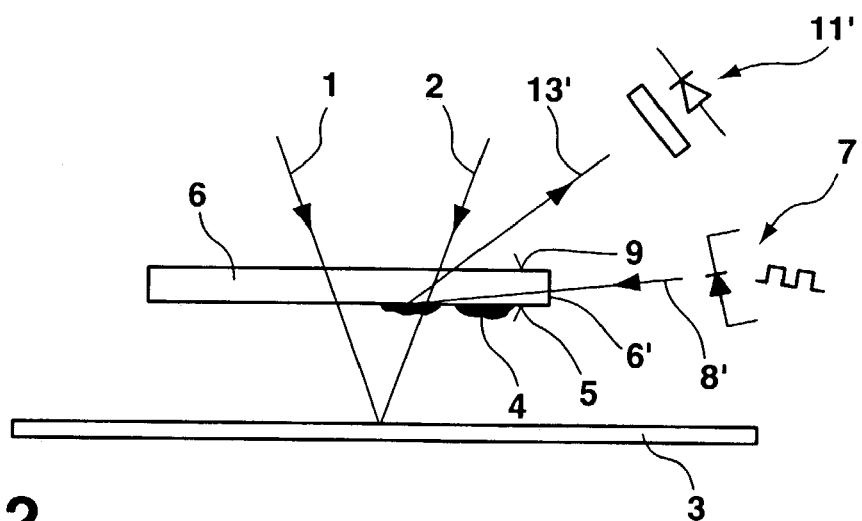
FIG. 2 is a side view of an apparatus for monitoring the deposit of splashes on an optical surface of a protecting glass of a laser processing machine.

In a modification of the arrangement of FIG. 1 according to FIG. 2, a light beam is coupled into a lateral edge or lateral surface (side face) 6' of the protecting glass 6. The soiling by deposit of splashes leads to a destruction of the surface of the protecting glass 6. The light beam 8' of the light source 7 is coupled into the edge 6' and is scattered on the destructed surface area of the protecting glass 6. As used here, reflection is a form of scattering. A detector 11' arranged with an angular top view is provided for monitoring a scattered light beam 13'. The intensity of the scattered light serves as a measure of the deposit of splashes.

Figure 3:
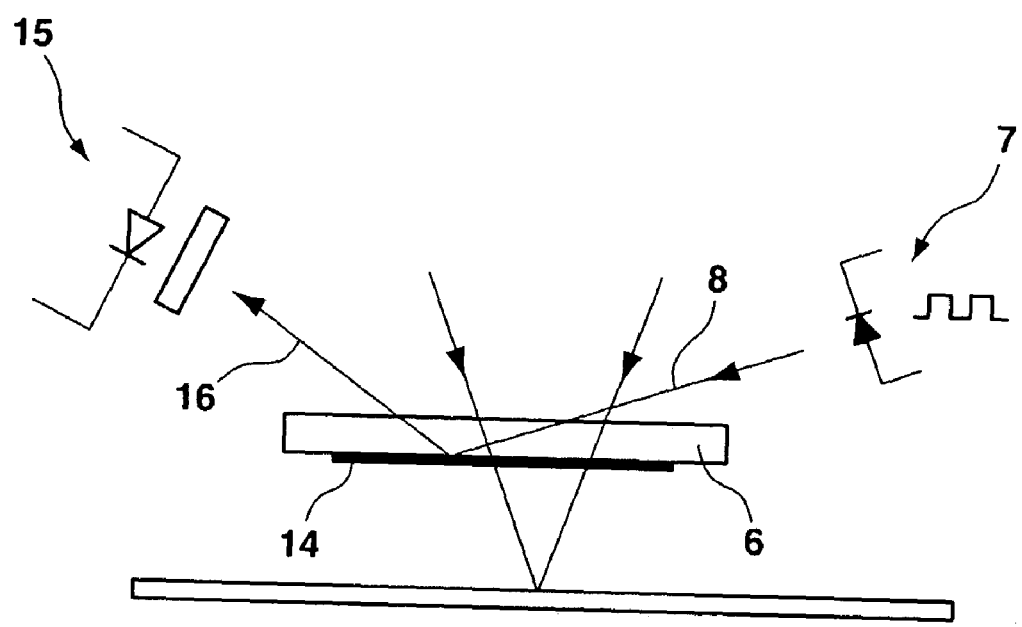
FIG. 3 is a side view of an apparatus for monitoring the formation of smoke on an optical surface of a protecting glass of a laser processing machine.

In an analog of the apparatus of FIG. 1, FIG. 3 shows a different deviation of the light beam 8 of the light source 7 after formation of smoke 14 on the optical surface. The smoke causes the light beam 8 to be reflected on the optical surface and leaves the protecting glass on the opposite optical surface. A correspondingly disposed detector 15 with upstream filter for YAG light can detect the reflected light beam 16. The intensity of the reflected light beam 16 can be evaluated as a measure of formation of smoke by downstream electronics to interrupt processing of the workpiece when a limiting value has been exceeded and replace the protecting glass 6.

Figure 4:
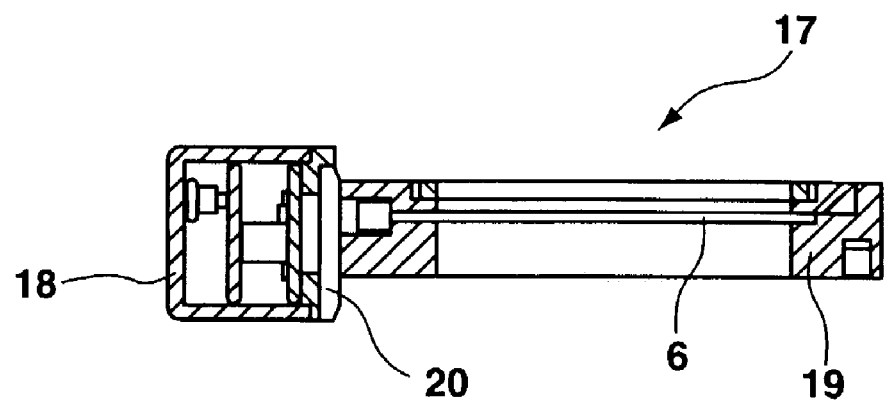
FIG. 4 is a longitudinal section through a cartridge for holding the protecting glass of a laser processing machine.
Figure 5:
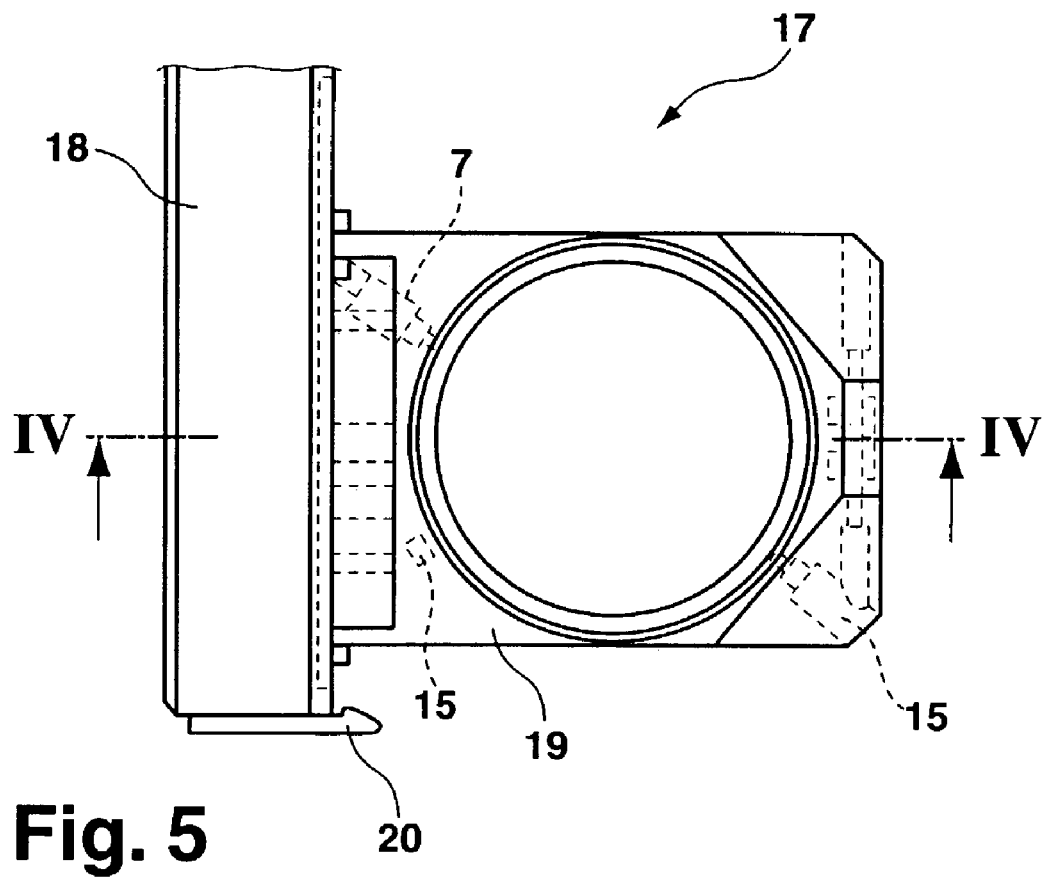
FIG. 5 is a top view of the cartridge of FIG. 4.

Referring to FIG. 4, to facilitate replacement of the protecting glass 6, the light source 7 adjusted to shine onto the protecting glass 6, and the detectors 11 and 15, and a cartridge 17 are provided that can be inserted into the processing head. The cartridge 17 consists substantially of a cartridge head 18 for convenient insertion and removal of the cartridge 17 and a cartridge insert 19 for holding the protecting glass 6. The cartridge insert 19 is characterized by a holder comprising a circular mounting or frame for the protecting glass 6. Only the protecting glass edge is supported on the mounting such that the protecting glass 6 is almost completely transparent for light beams. The protecting glass 6 can be inserted into the cartridge insert 19 and removed again. For stationary fixing of the protecting glass 6, a pivotable flap is provided for clamping the lateral protecting glass edge. The light source 7 and detectors 11 and 16 are adjustably fixed on the cartridge insert 19. The overall unit 17 can be inserted into and withdrawn from the processing head of the laser processing machine. The cartridge 17 can be inserted up to the cartridge head 18. A safety device in the form of a locking lever 20 locks the inserted cartridge 17 in a cavity of the processing head.

A number of implementations have been described. Nevertheless, it will be understood that various modifications may be made and are within the scope of the following claims.

What is claimed is:

1. An apparatus for monitoring an optical element of a processing head of a machine for thermal processing of a workpiece comprising:
   a first light source configured for coupling a first light beam into a first optical surface of an optical element and through the optical element, such that the first light beam is scattered from material deposited on a second optical surface of the optical element facing the workpiece; and
   a first detector configured and positioned for detecting a first portion of the first light beam scattered from material deposited on the second optical surface facing the workpiece.

2. The apparatus of claim 1, wherein the first optical surface into which the first light beam is coupled faces away from the workpiece.

3. The apparatus of claim 1, wherein the first detector is disposed on one side of the optical element and the light source is disposed on an opposite side of the optical element.

4. The apparatus of claim 1, wherein the first detector is disposed in proximity with the first optical surface on a side of the optical element opposite from the workpiece.

5. The apparatus of claim 1, further comprising a second detector configured for detecting a second portion of the first light beam scattered from material deposited on the second optical surface facing the workpiece.

6. The apparatus of claim 1, further comprising a second light source configured for coupling a second light beam into a third optical surface of the optical element, such that the second light beam is scattered from material deposited on the second optical surface of the optical element facing the workpiece.

7. The apparatus of claim 1 further comprising a cartridge adapted for insertion into and withdrawal from the processing head of the machine and adapted for holding the optical element, wherein the first light source and the first detector are disposed on the cartridge.

8. The apparatus of claim 7, further comprising electronics adapted for evaluating an intensity of the scattered light beam, wherein the electronics are disposed on the cartridge.

* * * * *